United States Patent [19]
Yukl

[11] Patent Number: 4,975,968
[45] Date of Patent: Dec. 4, 1990

[54] TIMED DIELECTROMETRY SURVEILLANCE METHOD AND APPARATUS

[75] Inventor: Tex Yukl, Baker, Oreg.

[73] Assignee: Spatial Dynamics, Ltd., Baker, Oreg.

[21] Appl. No.: 428,209

[22] Filed: Oct. 27, 1989

[51] Int. Cl.$^5$ .................... G06K 9/00; G01R 27/04
[52] U.S. Cl. ............................... 382/1; 324/647; 340/568
[58] Field of Search ............ 340/505, 568; 342/189; 374/130; 324/636, 640, 632, 642, 643, 644, 645, 646, 647; 382/1

[56] References Cited

U.S. PATENT DOCUMENTS

| | | | |
|---|---|---|---|
| 2,626,302 | 1/1953 | Schmitt | 175/183 |
| 2,744,235 | 5/1956 | Breit | 324/43 |
| 3,197,658 | 7/1965 | Byrnes et al. | 307/116 |
| 3,310,736 | 3/1967 | Bayly et al. | 324/62 |
| 3,412,381 | 11/1968 | Hirsch et al. | 340/164 |
| 3,518,551 | 6/1970 | Carniol et al. | 328/5 |
| 3,541,434 | 11/1970 | Mullen | 324/642 |
| 3,678,278 | 7/1972 | Peil | 250/106 R |
| 3,707,672 | 12/1972 | Miller et al. | 324/41 |
| 3,849,650 | 11/1974 | Patten | 250/321 |
| 3,868,626 | 2/1975 | Masher | 340/38 |
| 4,200,388 | 4/1980 | Hasebe et al. | 355/300 |
| 4,274,090 | 6/1981 | Cooper | 340/505 |
| 4,581,574 | 4/1986 | Goodman et al. | 324/647 |
| 4,686,517 | 8/1987 | Fockens | 340/572 |
| 4,720,701 | 1/1988 | Lichtblau | 340/572 |
| 4,777,478 | 10/1988 | Hirsch et al. | 340/573 |
| 4,779,077 | 10/1988 | Lichtblau | 340/572 |
| 4,782,342 | 11/1988 | Walton | 340/941 |
| 4,801,862 | 1/1989 | Osaki et al. | 324/632 |
| 4,813,564 | 3/1989 | Cooper et al. | 215/366 |

*Primary Examiner*—Leo H. Boudreau
*Assistant Examiner*—Tan Dinh
*Attorney, Agent, or Firm*—Kolisch, Hartwell & Dickinson

[57] ABSTRACT

Dielectrometry monitoring method and apparatus for three-dimensional profiling and colorable imaging of the material contents of articles carried on a conveyor through an interrogation region are disclosed. In a preferred embodiment, the apparatus includes a plural, stationary, collimated, microwave transmitter/receiver antennae array and associated electronics for measuring the dielectric constant of the materials to produce data for interpretation in real time as to the article's dielectric material configuration and contents. High-speed, GaAs gates and switching devices, as well as microstrip delay lines, are used to perform the precisely timed, depth-wise sampling of data reflective of dielectric-constant material characteristics, with sampling periods in the sub-nanosecond range. By comparison to predefined criteria, computerized analysis determines whether the data profile of the material within the interrogation region is indicative of any of a variety of contraband or hazardous conditions, including narcotic drugs and explosives. In the preferred embodiment of the invention, one each of such collimated arrays is positioned above and below the article-carrying conveyor in order to avoid potential blind spots that may be caused by conductive structures within an article.

4 Claims, 4 Drawing Sheets

TIMED DIELECTROMETRY SURVEILLANCE METHOD AND APPARATUS

BACKGROUND AND SUMMARY OF THE INVENTION

This invention relates generally to material surveillance method and apparatus. More particularly, it concerns the use of a serially energized, collimated microwave transmitter/receiver array to interrogate a region through which articles are conveyed to create an imageable, three-dimensional material nature and shape profile of real-time dielectric-constant conditions therein. The method and apparatus of the invention are described in the context of airport luggage surveillance systems for use in the detection of contraband or hazardous conditions.

Growing concern over airport and airline flight security against bomb threats and drug smuggling requires a diligent effort at improving the ability to screen luggage and interdict contraband. Traditionally, X-ray equipment has been used to provide a two-dimensional snapshot of the X-ray energy opacity of materials. It is capable of crudely discriminating between low- and high-density materials, i.e. it is useful in detecting high-metal-content items including most firearms. Three-dimensional X-ray screening equipment is not widely used, as it is prohibitively slow and costly, and requires multiple scanner arrays, mechanical scanning movement and substantial power. The high energy levels required for high-resolution X-ray scanning and the adverse, cumulative, physiological effects even of low-level X-radiation on living tissue require inordinate protective shielding measures. Even with proper shielding, there remains a significant health risk to operating personnel and to the public.

Ultrasound has found application in the medical arts, for fluid and soft body tissue boundary measurement and imaging. But ultrasound detection of contraband is impractical because the target materials are poor sonic media and because coupling ultrasonic energy to such materials is virtually impossible. Further, ultrasound lends itself better to sensing ultrasonic permeability changes in homogeneous materials, or boundaries between heterogeneous materials, than to classifying or identifying constituent materials.

Thermal neutron analysis represents a most recent advance in luggage scanning techniques. The technique depends upon bombardment of luggage with low-energy neutrons. The neutrons cause nitrogen, which is a constituent of most explosives, to emit gamma radiation that can be detected and analyzed by computer. It is reported that such equipment tends to render false-positive indications of explosives, due to commonly occurring high-nitrogen concentrations in wool, leather, plastics and foodstuffs. Thus, while this technique is sufficiently sensitive to detect, for example, plastic explosives, it is insufficiently selective to efficiently and accurately screen luggage. Of course, it is also extremely slow (requiring many seconds to screen each article), unsafe at any speed and limited to detection of materials that exhibit high nitrogen concentrations, which limitation renders it incapable of screening luggage for a wide variety of contraband material characteristics. Finally, because it is a new technology, thermal neutron analysis is very expensive, with present costs estimated to be an order of magnitude higher than conventional X-ray luggage screening.

As disclosed in my U.S. Pat. No. 4,234,844, issued Nov. 18, 1980, entitled "Electromagnetic Noncontacting Measuring Apparatus", it is possible to monitor electrical parameters by generating and focusing electromagnetic energy at a pair of electrically related, spaced focal points. According to the teachings of that patent, a bidirectionally focusing microwave antenna (as described in my companion U.S. Pat. No. 4,318,108, issued Mar. 2, 1982) can be used to interrogate living tissue by positioning one of its focal points adjacent an interrogation zone in a low-powered, non-contacting arrangement. By utilizing a receiver located adjacent the other focal point, it is possible, by monitoring voltage, current and phase conditions at the receiver, to determine related electrical conditions within the interrogation zone. One such electrical condition that has been found useful in medical monitoring and diagnosis is the dielectric constant of materials within the zone, as is described in my copending U.S. patent application Ser. No. 06/693,388, filed Jan. 22, 1985, entitled "Dielectric-Constant Change Monitoring", which issued as U.S. Pat. No. 4,947,848 on Aug. 14, 1990. These patent and patent application disclosures are incorporated herein by this reference.

It is a principal object of the invention to provide improved security/surveillance method and apparatus for use in luggage screening for contraband and/or hazardous condition detection.

Another object is to provide such method and apparatus that is capable of real-time, three-dimensional profiling and imaging of a wide variety of material contents of luggage.

It is still another object to provide such method and apparatus that uses a non-contacting, collimated array of bidirectionally focusing transmitter/receiver antennae defining an interrogation region through which articles are conveyed.

Yet another object is to provide a method for serially timed dielectrometric scanning of the nature and shape of material moving through an interrogation region.

It is also an object to analyze the timed dielectric response of materials to microwave energy incident thereon by computer analysis to identify contraband that may be within such materials.

Another object is to provide such method and apparatus that accurately and efficiently can screen for a variety of material types and amounts, with fewer false-negative and false-positive contraband indications than is possible with existing technologies.

It is a further object of the invention to provide such security/surveillance method and apparatus that may be operated safely and inexpensively.

These and other objects and advantages of the invention will become more fully apparent by reference to the following description and the accompanying drawings.

DETAILED DESCRIPTION OF THE PREFERRED EMBODIMENT

Figure 1:
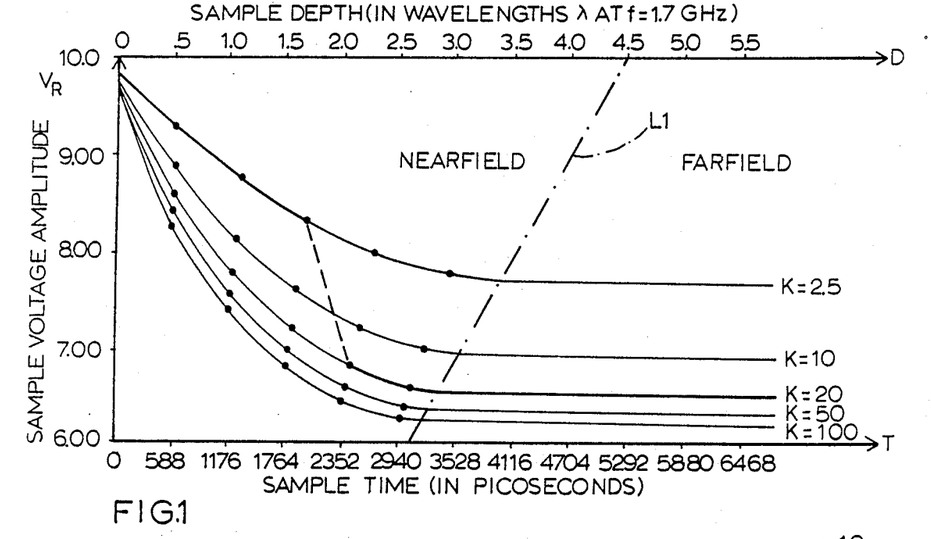
FIG. 1 is a graph showing a series of dielectric constant v. material depth curves that illustrate the timed dielectrometry method and apparatus of the invention.

Referring to FIG. 1, a voltage $V_R$ versus time T (and depth D) graph illustrates the principle of operation of the method and apparatus of the invention. A series of smooth curves represents characteristic timed dielectrometry measurements for materials having a range of dielectric constants K from 2.5 to 100, labeled as such. The curves do so by interpolating and extrapolating between and beyond successive, measured sample points represented as dots in FIG. 1. The ordinate of the graph represents energy received at a microwave antenna in response to energy transmitted thereby through materials located adjacent the transmitter portion of the antenna. The graph's abscissa represents the time at which the samples are received. The abscissa thus may be interpreted, based upon the operating microwave frequency of the antenna and well-known formulae, as the distance of the sample point from the aperture of the antenna, i.e. the depth D of the sample within the material being dielectrometrically monitored. Thus, timed dielectrometry refers to a quantified, time-based measure of the dielectric constant of materials through which microwave energy is made to propagate.

Every material possesses a characteristic dielectric constant. While all materials will cause the output, or reflected, voltage $V_R$ measured by the antenna to decrease exponentially with increasing depth D, each material will have an exponent identifiable to it. Measuring the reflected voltages that result from successively transmitting microwave energy through a variety of dielectrically homogeneous materials, each having a different, known dielectric constant, produces voltage versus time curves that characterize the dielectric constants of the materials, as shown in FIG. 1. Such standard, or characteristic, curves may be compared to voltage versus time curves derived from the monitoring of unknown materials to illuminate the contents of materials under interrogation.

A homogeneous material under interrogation would be expected to exhibit an exponential voltage versus time curve much like one of the series of curves shown in FIG. 1. Thus, the dielectric constant of the homogeneous material being monitored can be determined by simply comparing the measurement results with known standards. Because a material's dielectric constant substantially uniquely characterizes it, it is possible with a high level of accuracy and repeatability to determine the material's content.

A heterogeneous material under interrogation also would be expected to exhibit exponential voltage versus time curves like those of FIg. 1, but discontinuities would occur at dissimilar material boundaries. This phenomenon is illustrated in FIG. 1 as two broad, solid lines superimposed on the curves labelled "K=2.5" and "K=20" and joined by a dashed line. The broad, solid line to the left indicates the presence of material having a dielectric constant of two and one-half near the aperture of the antenna, i.e. at zero depth D. The broad, solid line to the right indicates the presence of material having a dielectric constant of twenty away from the aperture of the antenna. The broad, dashed line joining the two characteristically curved lines indicates the presence of a dissimilar material boundary at a distance of approximately 2λ in front of the aperture of the antenna, where λ represents the operating wavelength of the antenna. Thus, such a dielectrometric measurement as is represented by the broad lines of FIG. 1 yields a quantitative, depth-wise measure of a heterogeneous material's contents. This is the principle on which are based the method and apparatus of the invention.

Dash-dot line L1 in FIG. 1 delineates the boundary between the nearfield and farfield regions of the antenna. The timed dielectrometry surveillance method and apparatus of the invention are more effective in producing accurate dielectrometric measurements of materials lying in the nearfield region in front of the antenna's aperture. Thus, measured sample voltages to the left of L1 of the graph of FIG. 1 represent sufficiently accurate and repeatable, nearfield measurements that they may be used with confidence to dielectrically discriminate materials having, as indicated, a wide range of characteristic dielectric constants. The farfield region away from the antenna's aperture is not used in the practice of the invention in accordance with the preferred embodiment illustrated in FIG. 2. Those skilled in the art will appreciate that the effective depth of the timed dielectrometry method and apparatus is dependent upon the operating frequency f of the microwave transmitter/receiver, which may be varied from one application to another.

By way of introduction to the method and apparatus of the invention, certain terminology that is used herein will be explained. It will be understood that the following definitions apply:

site: a location of a single one of the collimated transmitter/receiver antennae within an array;

sample: a partial voltage measurement corresponding to received microwave energy at a given depth within the interrogation region at such site;

bit: five such samples representing a complete voltage measurement;

bar: five such bits at successive half-wavelength depths;

stack: n such bars representing a three-dimensional, cross-sectional slice of such complete voltage measurements, where n equals the number of sites in each collimated antennae array.

Those terms defined above that are used herein with some deviation from a commonly understood meaning within the associated arts, e.g. bit, bar and stack, will be demarked throughout by single quotes.

Figure 2:
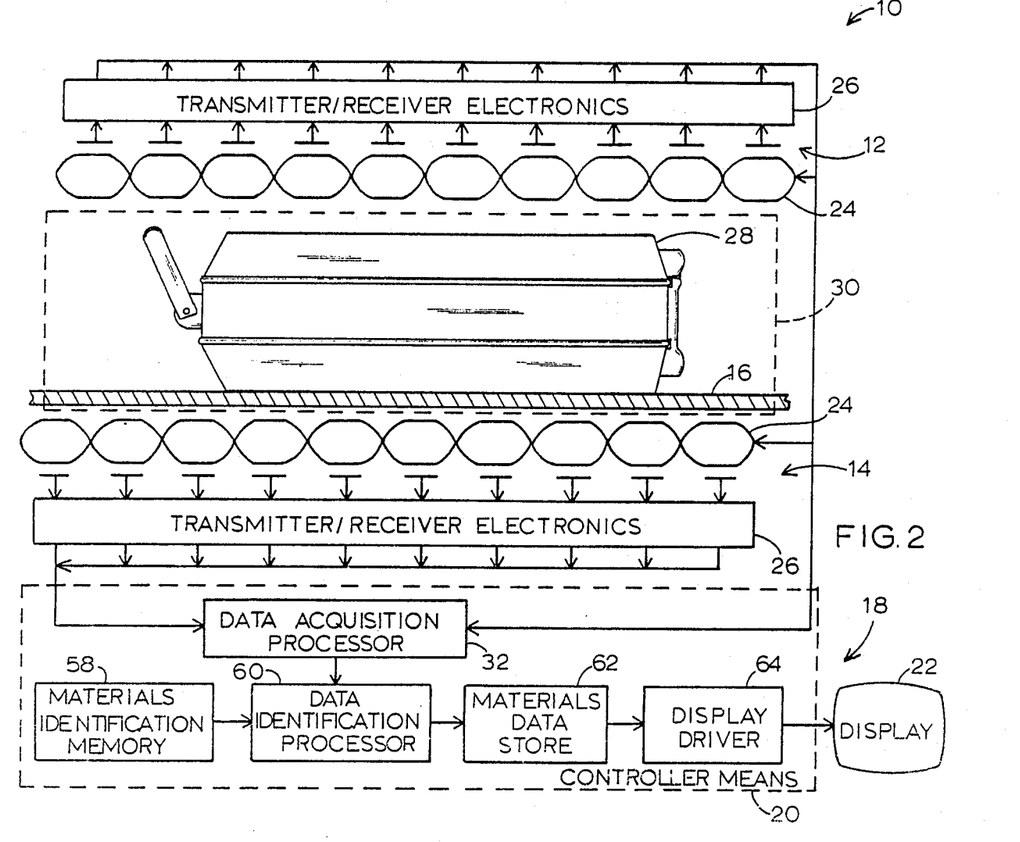
FIG. 2 is a combined schematic and physical system block diagram of the apparatus of the invention, made in accordance with its preferred embodiment.

Turning now to FIG. 2, article-scanning or surveillance apparatus for detecting characteristics of material moving through an interrogation region is shown at 10, in the form of a system block diagram, in a fragmentary, and partially schematic, end view. In its preferred embodiment, apparatus 10 includes serial electromagnetic transmission/reception means, or at least one of upper and lower dielectrometry monitors 12, 14 for interrogating the material contents of articles successively conveyed past a predefined location and through an interrogation region; an elongate conveyor 16 (shown in FIG. 2 in a fragmentary, end view); and means 18 connected with monitors 12, 14 for producing a three-dimensional material nature and shape profile in real time of changing dielectric conditions within the interrogation region. Means 18 preferably includes controller means 20 and annunciator means, or a display 22, for indicating in real time to a user of apparatus 10 the result of comparing predefined dielectric-constant indicia produced by controller means 20 to predefined dielectric-constant criteria stored therein. Monitors 12, 14 each includes plural antennae or transmitters/receivers, such as antenna 24, stationarily arrayed at the predefined location in a column and associated transmitter/receiver electronics 26. Each of monitors 12, 14 defines and in real time views what is referred to herein as an interrogation region containing successive, fractional volumes of articles or other material, such as luggage 28, moving or passing therethrough (along an axis normal to the plane of FIG. 2) on conveyor 16. A cross section of such an interrogation region is indicated generally in FIG. 1 by a rectangular, dashed outline 30. Controller means 20 includes a data acquisition processor 32, which will be described below in reference to FIG. 3. Not shown in FIG. 2 is means by which apparatus is suitably frame-mounted for the opposed, staggered alignment of monitors 12, 14; for the driving of conveyor 16; for the distribution of electrical power to the electronic components; and for the monitoring by an operator of display 22.

Figure 3:
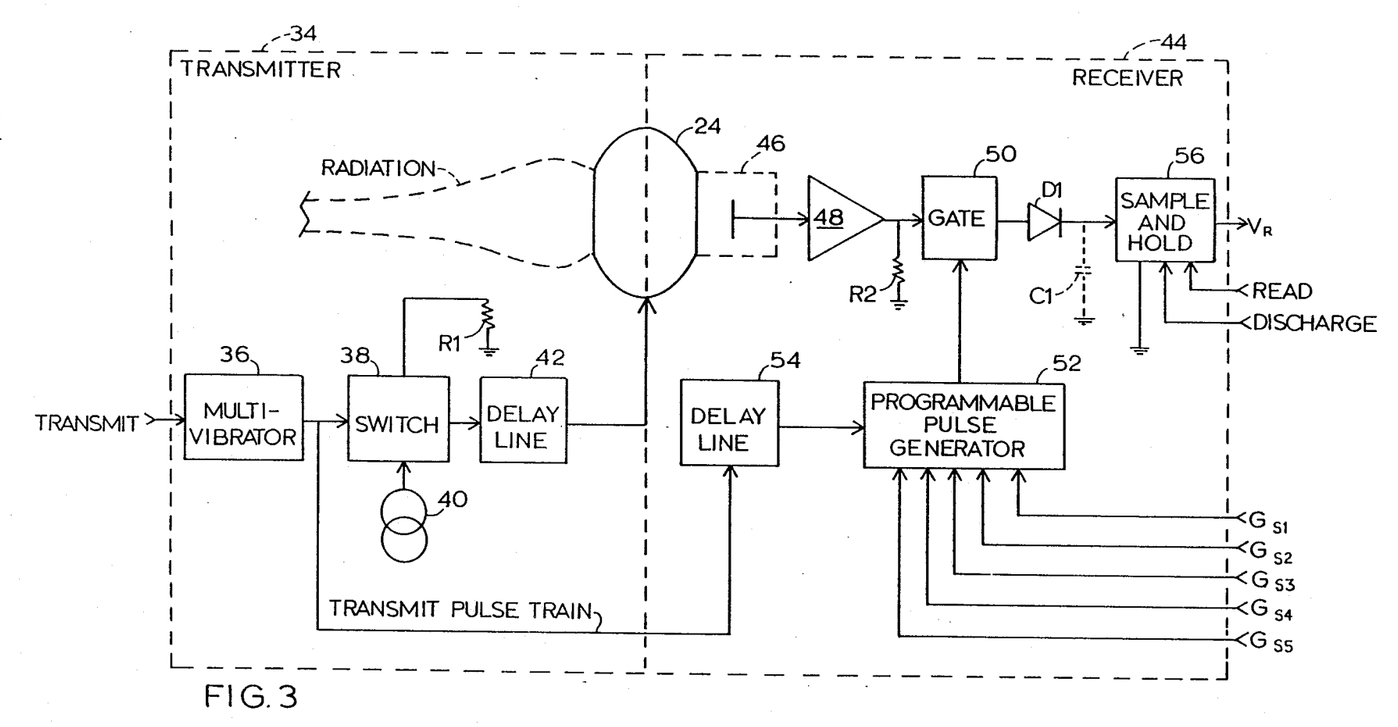
FIG. 3 is a schematic diagram of one of the antennae and associated transmitter/receiver electronics that form a part of the apparatus shown in FIG. 2.
Figure 4A:
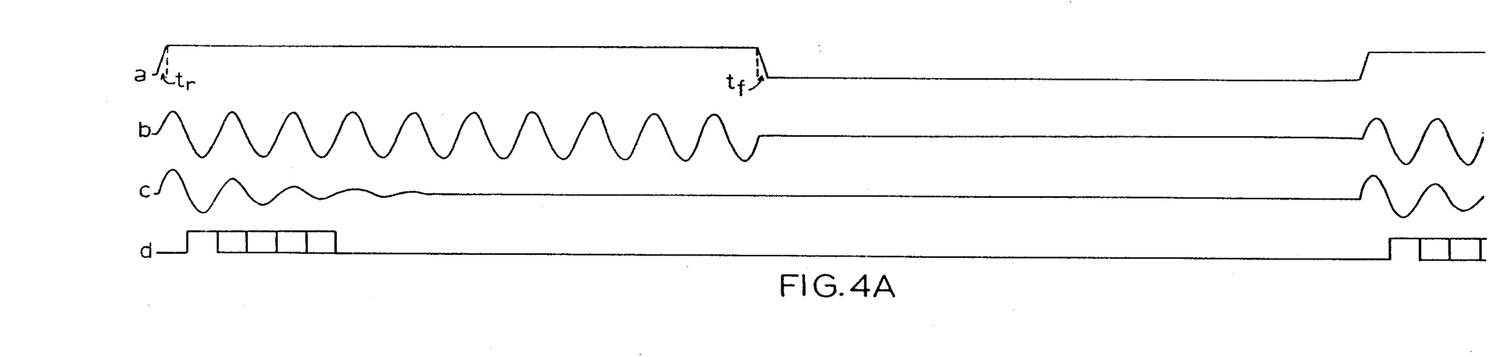
FIGS. 4A and 4B are a series of timing diagrams showing the relationships among certain signals produced by the apparatus of the invention.
Figure 4B:
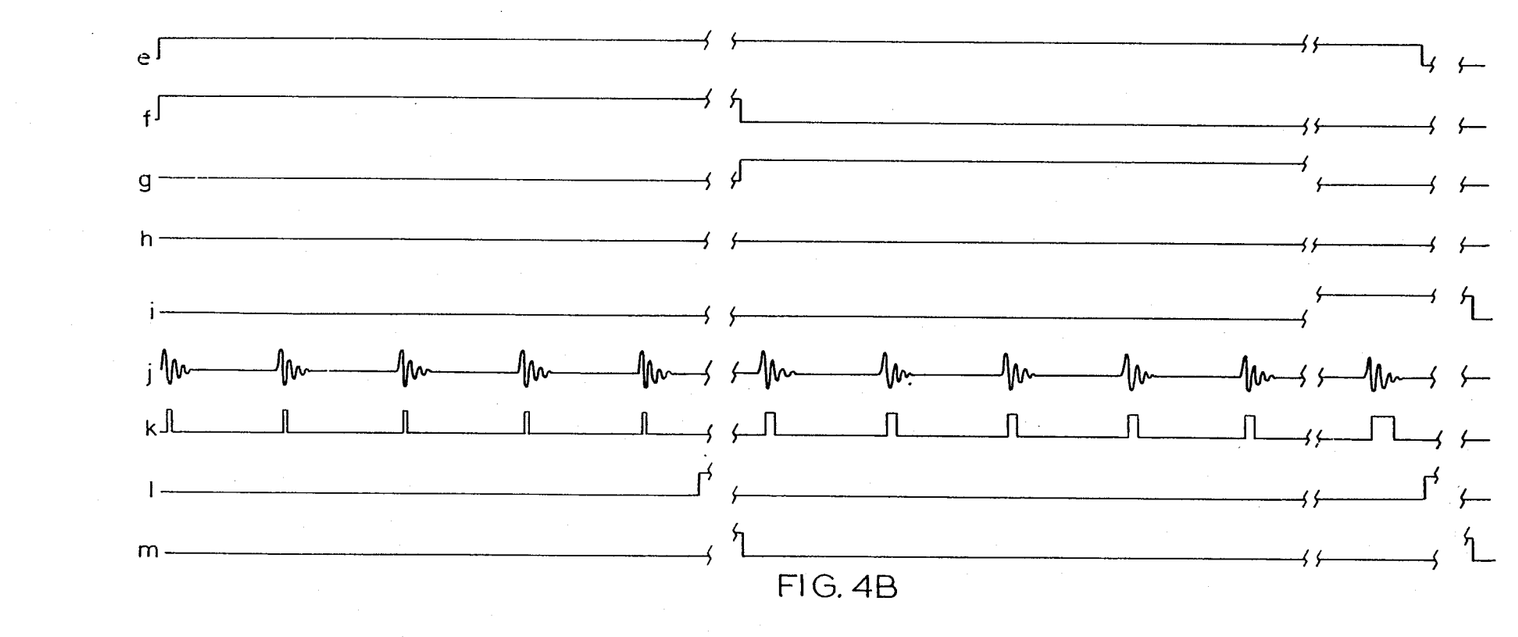

Referring collectively now to FIGS. 3, 4A and 4B, transmitter/receiver electronics that are associated with each of antennae 24, and their timing, will be described. It will be understood that the antenna and its associated circuitry shown in FIG. 3 are replicated, in the preferred embodiment of the invention, 2n times, where n is the number of antennae that are arrayed within each of monitors 12, 14. The timing of such circuitry will be seen to determine the accuracy and repeatability with which the materials moving through the interrogation region of apparatus 10 may be screened, which is why the circuitry is replicated for each antenna. But those of ordinary skill will appreciate that, within the spirit of the invention, certain signal paths and circuit components alternatively may be time-shared or multiplexed, or certain circuitry may be differently implemented or partitioned, thereby to simplify apparatus 10 and render it more cost-effectively manufactured, calibrated and maintained.

A transmitter 34 of transmitter/receiver electronics 26 includes a bistable multivibrator 36 that, upon command from data acquisition processor 32 via a signal TRANSMIT and for as long as TRANSMIT is active, produces a signal TRANSMIT PULSE TRAIN (shown in FIG. 4A at a). This signal controls the transmitter timing for dielectrometric measurements by each of the ten antennae of one of monitors 12, 14 shown in FIG. 2. In order to accommodate the high-frequency operation of microwave transmitter 34, TRANSMIT PULSE TRAIN must be made to transition from its active state to its inactive state at a very high rate. Thus, in the preferred embodiment of the invention, the leading edge of each pulse has a rise time t, of substantially less than 276-ps, and preferably less than approximately 60-ps. The trailing edge of each pulse preferably has a fall time $t_f$ of less than 300-ps. In order to provide adequate resolution along the axis of elongate conveyor 16, e.g. better than one inch resolution, at high conveyor speeds, e.g. greater than one foot per second (FPS), TRANSMIT PULSE TRAIN's repetition rate must be made relatively high. Preferably, each pulse of TRANSMIT PULSE TRAIN is active (high) for a period of time approximately equal to 5.58-ns and inactive (low) for a similar period of time. The importance of these timing requirements will be seen shortly.

It is this high-frequency transmit/receive rate, as well as the great volume of data that must be serially acquired and analyzed by transmitter/receiver 26 and controller means 20 in order to accomplish real-time, dielectrometric luggage surveillance, which imposes such timing requirements of TRANSMIT PULSE TRAIN. TRANSMIT PULSE TRAIN is used to control a high-speed, preferably GaAs-FET switch 38. One input to switch 38 is the output of a continuous, sine wave, varactor-tuned oscillator (VTO) 40. The other input to switch 38 is a DC reference, or blanking, voltage determined by the input leakage current of switch 38 through a resistor R1 to ground. The output of switch 38 is delayed by 588-ps through a microstrip delay line 42, which delayed, periodically oscillating output signal is used to energize antenna 24. In the preferred embodiment of the invention, VTO 40 outputs a 1.700-GHz sine wave. The result of switching the VTO's continuous output off and on by TRANSMIT PULSE TRAIN and delaying the switched output is that ten cycles of a relatively noise-free, 1.700-GHz sine wave are transmitted by antenna 24 for 5.8-ns, followed by an equal, 5.8-ns passive, or DC restoration, period of time (shown in FIG. 4A at b).

It will be understood that the plural antennae, such as antenna 24, are constructed in accordance with the teachings of my above-referenced U.S. Pat. No. 4,318,108, subject to the operating frequency, dimension, and configuration requirements of apparatus 10, as described herein. Each antenna 24 is capable of receiving a control signal from controller means 20 (as indicated in simplified, schematic form by a pair of directed, solid lines in FIG. 2) that causes it controllably to transmit and receive microwave energy. Each antenna 24 is capable of producing a response signal (as indicated by the directed, solid lines in FIG. 2) indicative of the dielectric constant of such material at successive depths therethrough. Thus, each antenna 24 that forms a part of monitors 12, 14 is capable of measuring the dielectric constant of the material within an article conveyed through interrogation region 30 (refer to FIG. 2). In the preferred embodiment of the invention, antennae 24 are approximately two inches in diameter and are closely spaced in a linear array, or column. It will be appreciated that, within the spirit of the invention, plural antennae, such as antenna 24, of apparatus 10 may be dimensioned, located and energized in a manner that achieves desirable monitoring span (aperture), range (depth) and resolution (horizontal and vertical) goals. The radiation profile of antenna 24 through a material of nominal dielectric constant is shown in FIG. 3 as a pair of generally converging, curved, dashed lines labeled RADIATION.

Referring still to FIGS. 3, 4A and 4B, a receiver 44 now is described in terms of its cooperation in transmitter/receiver electronics 26 with transmitter 34. A reference material 46 having a known dielectric constant approximately equal to the nominal, or average, dielectric constant of the target material is indicated generally by a dashed line in FIG. 3. Reference material 46 is placed adjacent the receiver aperture of antenna 24 such that it occupies a space embracing the receiver's focal point. Commencing at a predetermined time which corresponds to a distance $\lambda/2$, at a frequency f, after antenna 24 begins transmitting, reflected electromagnetic energy arrives at the focal point buried within reference material 46. Such reflected energy produces a received signal (shown in FIG. 4A at c and in FIG. 4B at j) that is amplified by an amplifier 48, biased by a resistor R2 and input to a high-speed, preferably GaAs switch, or gate 50. Gate 50 is controlled by a programmable pulse generator 52 variably periodically to pass the amplified, received signal to its output. There it is rectified by a high-speed, low-forward-voltage-dropping diode D1, e.g. a zero-bias Schottky diode.

First microstrip delay line 42 of transmitter 34 establishes a precisely controllable and repeatable delay that is sufficient to permit delay compensation, via a second microstrip delay line 54, of the timing of pulse generator 52. During five successive pulses of TRANSMIT PULSE TRAIN, generator 52 (the output of which is shown in FIG. 4A at d and FIG. 4B at k) opens gate 50 for a predetermined period of time to permit the net capacitance between the cathode of diode D1 and the input of a sample and hold circuit 56 (indicated in dashed lines as C1 of FIG. 3) to charge to the level of the received, amplified voltage at the anode of diode D1. Sample and hold circuit 56 is READ and then DISCHARGEd under the control of data acquisition processor 32 to permit sampling and analogue-to-digital conversion of the peak voltages $V_R$ of successive, half-wave excursions of the received, amplified signal.

Five such samples are taken for each of five data 'bits' representing successive, $m\lambda/2$-deep (for m from 1 to 5) volumes of material in front of the aperture of antenna 24 and within interrogation zone 30 (refer to FIG. 2). Delay line 54 is made to establish the precisely controllable and repeatable opening of gate 50 at the time that the received, amplified energy at the anode of diode D1 begins its first negative-going, half-sine wave excursion (the first positive-going, half-sine wave excursion containing only incident, and no reflected, microwave energy). Signals $G_{S1}$, $G_{S2}$, $G_{S3}$, $G_{S4}$, $G_{S5}$ are controlled by data acquisition processor 32 to program pulse generator 52 with the appropriate R-C time constant, e.g. by the use of a PIN diode array, for the acquisition of successive 'bits.' This is accomplished by opening gate 50 for incrementally longer times after each sample is read by data acquisition processor 32.

In accordance with the preferred embodiment of the invention, successive 'bits' are sampled by opening gate 50 for 588-ps, 1.176-ns, 1.764-ns, 2.352-ns and 2.940-ns (refer to FIG. 4A at d and FIG. 4B at k) to produce what will be referred to herein as site data. The reason for opening gate 50 for progressively increasing periods of time--rather than opening it for a constant period of time coinciding with each of the succesive half-sine wave excursions--is to render the timing more accurate and repeatable. Accordingly, in the preferred embodiment of the invention, successive openings of gate 50 are referenced uniformly to the precisely controlled leading edge of each pulse within TRANSMIT PULSE TRAIN, and successive closures of gate 50 are delayed relative to such referenced leading edge by high-precision R-C-produced time constants. The result of this variable-period gating of received microwave energy in receiver 44 will be referred to herein as volume-fraction weighting, the effect of which will be discussed below. The five-'bit' site data-producing process is repeated 2n times, once for each site, e.g. twenty times in accordance with the embodiment of the invention illustrated in FIG. 2. Finally, site data from monitors 12, 14 are correlated by known techniques, based upon the location of each site relative to each other, so as to represent a three-dimensional cross section of the material contents of interrogation region 30.

Turning specifically now to FIGS. 4A and 4B, the timing relationships among many of the signals produced by controller 20, transmitter 34 and receiver 44 will be summarized. First, it is noted that FIGS. 4A and 4B are not of the same horizontal time scale. FIG. 4A (which is continuous) represents a lapse of approximately 12-ns, whereas FIG. 4C (which is fragmentary) represents a lapse of at least 300-ns, depending upon the speed with which data acquisition processor 32 can toggle TRANSMIT, select $G_{S1}$ through $G_{S5}$, and READ and DISCHARGE sample and hold circuit 56. The signal waveforms of FIGS. 4A and 4B may be described as follows (refer to the above description of the operation of transmitter 34 and receiver 44 in reference to FIG. 3):

a—TRANSMIT PULSE TRAIN (output of multivibrator 36);
b—transmitted microwave energy (output of delay line 42);
c—received microwave energy (output of amplifier 48);
d—sample gate control (control input to gate 50);
e—TRANSMIT (input to multivibrator 36);
f—$G_{S1}$ (input to programmable pulse generator 52);
g—$G_{S2}$ (input to programmable pulse generator 52);
h—$G_{S3}$, $G_{S4}$ (inputs to programmable pulse generator 52);
i—$G_{S5}$ (input to programmable pulse generator 52);
j—received microwave energy (input to amplifier 48);
k—sample gate control (control input to gate 50);
l—READ (input to sample and hold circuit 56);
m—DISCHARGE (input to sample and hold circuit 56).

Those of ordinary skill in the art will appreciate that the breaks between fragments of the signals shown in FIG. 4B indicate a lapse of time during which, for example, data acquisition controller 32 processes input signals, and generates output signals responsive thereto. In accordance with the preferred embodiment of the invention in which data acquisition controller 32 is a high-speed microprocessor, relatively significant time nonetheless may elapse during such breaks, depending upon analogue-to-digital conversion and instruction execution rates. The scanning of monitors 12, 14 to produce a single 'bar' of received microwave energy from transmitter/receivers 26 typically will require substantially more time than 300-ns. Nevertheless, the important high-speed timing requirements of transmitters/receivers 26 are realized by the hardware implementation illustrated in FIG. 3. Thus, the speed of the data acquisition process affects only the data acquisition rate (not its accuracy or repeatability), and, consequently, affects only the article-scanning rate (throughput) of apparatus 10, which may be many articles per second, or an order of magnitude improvement over prior art techniques. The operation of data acquisition processor 32 may be synchronized with the operation of conveyor 16 to produce medium-resolution 'stack' data representing time slices of the dielectric constants of the contents of material within interrogation region 30 at any given time during the continuous travel of conveyor 16 therethrough.

Summarizing the operation and timing of transmitter/receiver electronics 26 in reference to FIGS. 2, 3, 4A and 4B, ten cycles of a 1.700-GHz sine wave are used to energize transmitter 34, followed by an equal DC restoration period to ensure that no prior energizing period's reflected data is present at receiver 44. Five peak excursions of the received, amplified, rectified signal corresponding to a one-half-wavelength depth in front of the antenna's aperture are sampled, held and read (e.g. via the READ signal shown in FIG. 4B at 1) by receiver 44 and data acquisition processor 32, and then are discharged (e.g. via the DISCHARGE signal shown in FIG. 4B at m). The greatest of these five peak excursions is held by sample and hold circuit 56, and is interpreted by data acquisition processor 32 as a single data 'bit' at a given depth. The five-sample process is repeated five times (as shown fragmentarily in FIG. 4B), with incrementally longer gating times, to obtain five data 'bits', or a 'bar' of data, representative of the exponentially decreasing, reflected voltage at successive half-wavelength material depths in front of the aperture, to the 2.5-wavelength extent of the antenna's nearfield effectiveness ("nearfield range"). The five-'bit' process is repeated $2n$ times in succession, where $n$ equals the number of antennae, or sites, in each of monitors 12, 14. Thus, twenty-five pulses of TRANSMIT PULSE TRAIN are required to produce five 'bits' of data representing the depth-wise dielectric constant profile of material contents within the view of a single antenna, or site.

Referring again to FIG. 2, controller means 20 now will be described in some detail. Controller means 20 produces a control signal to each of antennae 24 within the antennae arrays, or within monitors 12, 14 (as indicated in simplified, schematic form by a pair of directed, solid lines in FIG. 2). Controller means 20 also receives response signals therefrom (as indicated by plural directed, solid lines in FIG. 2). Controller means 20 includes correlation means, which forms a part of data acquisition processor 32, for correlating the control signals with corresponding response signals in the time domain, as described above in reference to FIGS. 3, 4A and 4B. By producing such control signals to antennae 24 and receiving such response signals therefrom, and by correlating the former with the latter, controller means 20 produces so-called depth-dependent dielectric-constant indicia of the material within an article passing through interrogation region 30.

In the preferred embodiment of the invention, controller means 20 includes, in addition to data acquisition processor 32 and its correlation means, a materials identification memory 58, a data identification processor 60, a materials data store 62 and a display driver 64. Materials identification memory 58 and materials data store 62 are referred to collectively herein as data storage means for storing (1) predefined dielectric-constant criteria based upon characterized standard, or reference, materials, and (2) dielectric-constant indicia produced by data acquisition processor 32. It will be understood that the blocks illustrated as forming a part of controller means 20 are functional, rather than physical, blocks. Those skilled in the art will appreciate that such functions as are described below may be implemented in a variety of ways. For example, a single, multitasking, high-speed microprocessor may perform all required functions under the control of a read-only memory-based software program. Or discrete, hardware circuitry may generate the output signals and monitor the input signals required to control transmitter/receiver electronics 26 and display 22. In the preferred embodiment, a combination of hardware and software performs the functions of controller means 20.

In accordance with the preferred embodiment of the invention, data acquisition processor 32 generates such control signals as are necessary to command transmitter 34 to transmit microwave energy, e.g. TRANSMIT (refer to FIG. 4B at e), and to receive successive 'bits' of sampled data from receiver 44, e.g. $G_{S1}$, $G_{S2}$, $G_{S3}$, $G_{S4}$, $G_{S5}$ (refer to FIG. 4B at f through i), READ (refer to FIG. 4B at 1) and DISCHARGE (refer to FIG. 4B at m), in accordance with the timing requirements described above in reference to Fig. After acquiring five 'bits' of data from transmitter/receiver electronics 26 for each site at which an antenna is located, data acquisition processor 32 invokes data identification processor 60. After invoking data identification processor 60, and passing thereto the acquired data for identification, data acquisition processor 32 is free to repeat the data acquisition process on the next 'bar' of data, i.e. one corresponding to another site within monitor 12 or 14. Once data acquisition processor has scanned all sites, e.g. twenty in accordance with the preferred embodiment of the invention, it starts over again with the scanning of interrogation region 30 that now contains a material volume that has been continuously advanced along conveyor 16 in a direction normal to the plane of FIG. 2.

While data acquisition processor 32 is controlling the serial scanning operation of transmitter/receiver electronic 26 and antennae 24 of monitors 12, 14, data identification processor 60 compares data gathered in a previous scanning operation to data within materials identification memory 58. Data identification processor 60 is referred to herein as comparison means for comparing predefined dielectric-constant criteria stored in material identification memory 58 with dielectric-constant indicia produced by data acquisition processor 32 to produce a comparison result. As was suggested in reference to FIG. 1, if successive data 'bits' for a given site describe a single, exponentially decaying curved line that corresponds to a characteristic curve stored in materials identification memory 58, then it may be concluded with substantial certainty that the material within the interrogation region and in view of the antenna at that site is homogeneous and of a dielectric constant corresponding to that of the material characterized by the stored criteria. If successive data 'bits' for a given site describe more than one exponentially decaying curved line, then it may be concluded that there are at least two dielectrically distinguishable materials within view of the antenna at that site. If corresponding data 'bits', i.e. 'bits' corresponding to the same depth or distance from the antennae's receiver apertures, for adjacent sites describe different exponentially decaying curved lines, then it may be concluded that the materials within the views of the adjacent antennae are dielectrically distinguishable.

Those skilled in the art will appreciate that the material-recognition sensitivity of apparatus 10 is greatest closest to the antennae's apertures. This is because of the so-called volume-fraction weighting that results from opening gate 50 for progressively longer periods of time in the successive sampling of 'bits.' Nevertheless, dielectrically dissimilar material boundaries are discernable throughout the nearfield range by comparison of sampled data 'bits' with data in materials identification memory 58, to the approximately one inch horizontal resolution and the approximately one-half inch vertical resolution of apparatus 10 (corresponding the the horizontal and vertical aspects of FIG. 2). Also, the contents of material within the interrogation region are identifiable by comparison to what may be thought of as a library of material dielectric-constant characteristics.

In the preferred embodiment of the invention, data identification processor 60 classifies the five 'bits' of data obtained from each site as falling within a range of dielectric constants to which a color may be assigned, e.g. blue for $1 \leq K \leq 3$; yellow for $4 \leq K \leq 7$; red for $8 \leq K \leq 11$; orange for $12 \leq K \leq 15$; violet for $16 \leq K \leq 19$; green for $20 \leq K \leq 25$; black for $26 \leq K \leq 49$; and white for $K \leq 50$. Data identification processor 60 then stores in materials data store 62 a color code for each 'bit', along with the 'bit' number, site and a "HAZARD" alert status indication, or flag, based upon the known dielectric constants of hazardous materials. Once the identification data for a single 'bar' have been produced and stored in materials data store 62, data identification processor 60 is free to analyze another 'bar' of data from data acquisition processor 32. The inability of data identification processor 60 to render a favorable comparison also may be flagged to indicate that the identification results are suspect.

Materials data store 62 is preferably of dual-access or partitioned memory architecture that provides write access to data identification processor 60 and read access to display driver 64 of a color display buffer maintained therein. Materials data store 62 is used by display driver 64 to produce a colored, two-dimensional representation of the dielectric contents of interrogation region 30 on color display 22. A variety of imaging and display technologies are available for use in surveillance apparatus 10. Depending upon the operating frequency f of transmitter 34 and the actual dielectric constant of the materials radiated thereby, apparatus 10 may require only low to moderate display resolution. For example, it may be that display driver 64 may be integral with display 22, in the form of a flat-panel, liquid crystal display.

Those skilled in the art will appreciate, however, that within the spirit of the invention, display 22 may be made to display more or less than simple, two-dimensional material profile data, or color images of 'stacks' that correspond to interrogation region 30. For example, display 22 may provide so little as a go/no-go indication to the operator as to the absence/presence of contraband or a hazardous condition. Alternatively, display 22 may provide so much as an enhanced, high-resolution, colored image reflective of the three-dimensional material configuration and contents of the portion of an article embraced by interrogation region 30. Display 22 may even provide a pseudo-three-dimensional representation of the material contents of an entire article (by well-known buffering and image-enhancement techniques). Thus, display 22 is referred to herein generally as annunciator means for indicating in real time to a user of apparatus 10 the result of comparing timed dielectric-constant indicia with predefined criteria.

Materials identification memory 58, data identification processor 60 and materials data store 62 may be thought of as interpretation means that, when coupled with transmission/reception means comprising monitors 12, 14 and data acquisition processor 32, is responsive to serial reflections of electromagnetic energy from articles conveyed through an interrogation region. When operated in accordance with the illustrated embodiment of the invention described immediately above, apparatus 10 produces imageable profile data reflective of the material configuration and contents of such articles within interrogation region 30.

Figure 5A:
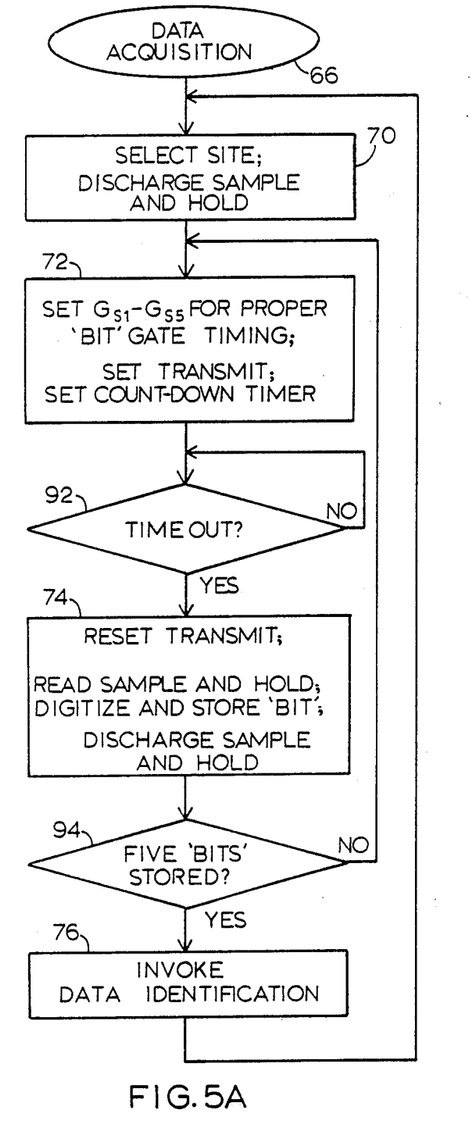
FIGS. 5A and 5B are a flowchart illustrating the data and control flow implemented by the controller shown in FIG. 2.
Figure 5B:
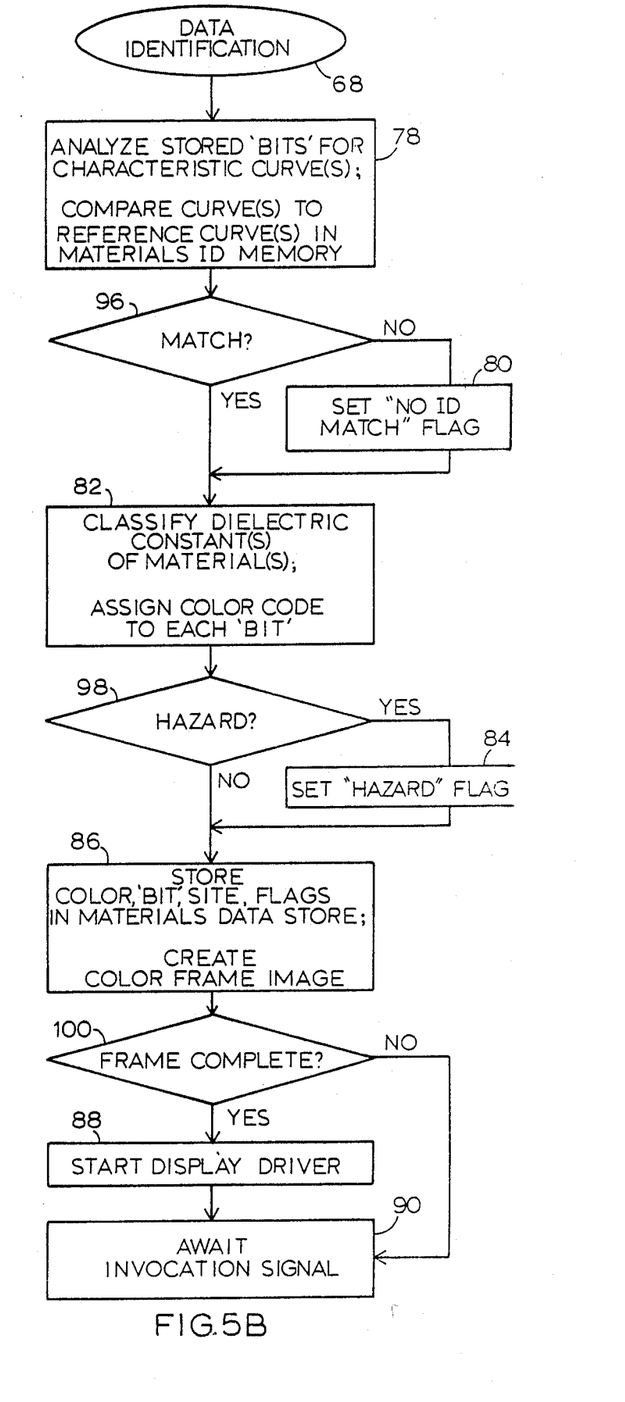

Turning now to FIG. 5, the acquisition, identification, storage and display of data by controller means 20 will be described by reference to a flowchart. It will be appreciated that diagramming conventions have been adopted, including a generally top-to-bottom and left-to-right directional flow. Ellipses indicate starting points of processes (e.g. starting points 66, 68). Rectangles indicate task or action blocks (e.g. action blocks 70, 72, 74, 76, 78, 80, 82, 84, 86, 88, 90). Rhombuses indicate decision blocks (e.g. decision blocks 92, 94, 96, 98, 100), with the answers to the enclosed questions determining the decisional paths next to be taken. The flowcharts of FIG. 5 are quite self-explanatory to those of ordinary skill in the pertinent art, and will not be discussed in detail. It will be understood by those skilled in the art that the illustrated processes may be implemented in software, firmware, hardware or a combination thereof.

Referring first to FIG. 5A, which charts the data acquisition process, it is noted that a count-down TIMER that is set at 72 and tested at 92 controls the duration of the TRANSMIT command to transmitter 34 (refer to FIG. 3), which accommodates the acquisition of five samples for each 'bit.' In accordance with the preferred embodiment of the invention, TIMER must count down for a period of time greater than or equal to 58.8-ns, i.e. the duration of five pulses of TRANSMIT PULSE TRAIN. It is noted that the illustrated steps are performed once for each site, or antenna, within monitors 12, 14 (refer to FIG. 2), in order to scan an entire 'stack.' Thus, data identification is invoked at 76, e.g. by signalling, each time it is determined that five 'bits' have been stored. Thereafter, successive sites are selected, and the illustrated steps of the data acquisition process are repeated.

Referring next to FIG. 5B, it is noted that data identification begins when invoked by the data acquisition process at 76, and continues thereafter concurrently with further data acquisition. It is also noted that, after analyzing, or curve-fitting, the sampled data 'bits' for each site, relative to the reference materials curves stored in materials identification memory 58, the data identification process determines at 96 whether there is a match, i.e. whether the sampled 'bits' represent recognizable dielectric material contents. If no match is found, potentially indicating the presence within interrogation region 30 of material outside the recognizable dielectric-constant ranges, a flag is set to indicate to the operator that "NO ID MATCH" has been found at some 'bit' location within the present 'bar'. Conversely, if a material within a recognizable dielectric-constant range is indicated as containing contraband or a hazardous condition, then a flag is set to indicate to the operator that a "HAZARD" has been found at some 'bit' location therewithin. A color frame image buffer incrementally is created as each site's data are analyzed, classified and stored in materials data store 62. Once a single scan of all antennae 24 within monitors 12, 14 has been completed, as determined at 100, display driver 64 is started. Thereafter, successive, correlated 'stack' pairs, or cross sections representing the color-coded, two-dimensional image of a approximately one-inch slice of the three-dimensional material configuration and contents of articles transported by conveyor 16 through interrogation region 30, may be viewed on display 22.

In summary, apparatus 10 now is understood to comprise, in its preferred embodiment, upper and lower monitors 12, 14 located in laterally offset relationship with one another and oriented in opposition to one another, thereby to define interrogation region 30 through which luggage 28 passes on conveyor 16. It will be appreciated that, within the spirit of the invention, one monitor only may be used, and it may define an interrogation region either above or below it. The effective height of interrogation region 30 is determined by the operating frequency f of the antennae and the approximately 2.5-wavelength extent of the nearfield range in which such antennae are most effective to produce accurate, repeatable dielectric-constant indicia. It will be understood that the effectiveness of apparatus 10 in screening articles is somewhat dependent upon the nature of the material contents within interrogation region 30. This is because the antennae are 'blind' in an area behind materials of certain size, orientation and conductivity, e.g. a small piece of wire. In order for each of monitors 12, 14 to view the interrogation region, including any locations therein to which the other might be 'blind', monitors 12, 14 of the preferred embodiment of the invention illustrated in FIG. 2 are positioned closely to, and directed oppositely from, one another. It will be understood that, in such an embodiment, opposing antennae are susceptible to radiation from one another. Thus, the energizing of each antenna may be separated in time, as in the preferred embodiment by the timing illustrated in FIG. 4 and the control illustrated in FIG. 5, to avoid illumination by another. Of course, within the spirit of the invention, other techniques may be used, e.g. frequency shifting, to avoid inter-monitor data contamination.

In accordance with the preferred embodiment, apparatus 10 defines an interrogation region that is approximately equal to its nearfield range in height, or approximately six inches (refer to FIG. 2). Apparatus 10 is of virtually unlimited width, which is determined by the number n of antennae within each of monitors 12, 14. In accordance with the preferred embodiment, monitors 12, 14 are laterally offset by one-half of the diameter of an antenna 24. By decreasing the vertical separation of monitors 12, 14 approximately to equal the nearfield range of antennae 24 and by providing data acquisition processor 32 with means for smoothing, as well as correlating, the resultantly overlapping site data, the horizontal resolution of apparatus 10 is increased. Because its plural, collimated antennae are stationarily arrayed, apparatus 10 has no moving parts (other than conventional conveyor 16). Thus, apparatus 10 can be manufactured relatively inexpensively, and requires relatively less maintenance than luggage-scanning apparatus that depends upon mechanical scanning movement. The low energy, e.g. $<1\text{-}\mu W/cm^2$ (in air), and high frequency, e.g. 1.700-GHz, levels at which apparatus 10 operates render it safe and energy efficient in surveillance contexts, whether it is used to complement other surveillance equipment, e.g. X-ray equipment, or in a stand-alone environment.

The method, as well as the apparatus, of the present invention now may be understood. The timed dielectrometry surveillance method includes conveying articles in succession past a predefined location as by conveyor 16. It further includes interrogating a region at the predefined location, e.g. interrogation region 30, through which successive articles are being conveyed by projecting microwave energy from plural collimated transmitters/receivers, e.g. arrayed antennae 24 and their associated transmitter/receiver electronics 26, and measuring reflected energy responsive thereto. These steps are performed in such manner that the projecting and measuring are accomplished sequentially, e.g. under the control of data acquisition processor 32 across such transmitters/receivers, with the interrogating step producing timed indicia, e.g. successive samples and 'bits', of the dielectric constant of material within the interrogation region. The method also includes the important step of comparing, e.g. by data identification processor 60, such indicia with predefined criteria, e.g. those stored in materials identification memory 58, to characterize the material contents of an article passing through the interrogation region. Finally, the preferred method of the invention includes annunciating, or indicating in real time to a user of the apparatus of the invention, the result of such comparing step.

Accordingly, while a preferred method for practicing the invention, and a preferred embodiment of the apparatus of the invention, have been described herein, it is appreciated that virtually unlimited modifications are possible that come within the scope of the invention.

It is claimed and desired to secure by Letters Patent:

1. For detecting characteristics of material moving through an interrogation region, surveillance apparatus comprising:
   a dielectrometry monitor that defines a generally planar interrogation region and in real time views said interrogation region and material moving therethrough generally normal to the plane of the interrogation region, and
   means synchronized with such movement of the material through the interrogation region and operatively connected with said monitor for producing a three-dimensional material profile in real time of changing dielectric conditions within said interrogation region.

2. For use in a surveillance system having an elongate conveyor for conveying articles successively past a predefined location, article-scanning apparatus comprising:
   serial electromagnetic transmission/reception means defining an interrogation region for interrogating the material contents of articles successively conveyed past a predefined location and through said interrogation region, and
   interpretation means coupled with said transmission/reception means, said interpretation means being responsive to serial reflections of electromagnetic energy from such articles, thereby to produce imageable profile data reflective of the material configuration and contents of such articles within said interrogation region.

3. A timed dielectrometry surveillance method comprising:
   conveying articles in succession past a predefined location;
   interrogating a region at the predefined location through which successive articles are being conveyed, said interrogating including projecting microwave energy from plural collimated transmitters/receivers and measuring reflected energy responsive thereto, wherein said reflected energy is dependent upon the dielectric constant of material within the interrogation region, said projecting and said measuring being performed sequentially across said plural collimated transmitters/receivers, said interrogating producing timed indicia of the dielectric constant of material within the interrogation region; and comparing said dielectric constant indicia with predetermined criteria to characterize the material contents of an article passing through the interrogation region.

4. For use in a surveillance system having an elongate conveyor for conveying articles successively past a predefined location, article-scanning apparatus comprising:

plural antennae stationarily array ed at the predefined location, said antennae being arrayed such that they define an interrogation region through which an article on a conveyor will pass, each of said antennae being capable of measuring the dielectric constant of the material within an article and producing a response signal indicative of the average dielectric constant of such material at successive depths therethrough;

controller means for producing a control signal to each antenna within said antennae array, and for receiving a corresponding response signal produced by each antenna within said antennae array, said controller means including means for time-correlating said control signal with said corresponding response signal, thereby to produce depth-dependent dielectric-constant indicia of such material within said interrogation region, said controller means further including data storage means for storing predefined dielectric-constant criteria and for storing said indicia, said controller means further including comparison means for comparing said predefined criteria with said indicia to produce a comparison result; and annunciator means for indicating in real time to a user of said apparatus said comparison result.

* * * * *